United States Patent [19]

Ocamb et al.

[11] Patent Number: 6,133,196
[45] Date of Patent: Oct. 17, 2000

[54] BIOLOGICAL CONTROL OF PLANT DISEASE ON ROOTS OF CONIFER SEEDLINGS

[75] Inventors: Cynthia M. Ocamb, St. Paul; Cynthia Buschena, New Brighton, both of Minn.

[73] Assignees: Regents of the University of Minnesota, Minneapolis, Minn.; The United States of America as represented by the Secretary of Agriculture, Washington, D.C.

[21] Appl. No.: 08/696,048

[22] Filed: Aug. 13, 1996

[51] Int. Cl.[7] .......................... A01N 63/00; A01N 63/02; A01N 63/04; C12N 1/14

[52] U.S. Cl. ..................... 504/100; 504/117; 424/93.3; 424/93.4; 424/93.43; 424/93.47; 424/93.5; 47/DIG. 9; 435/911

[58] Field of Search ..................... 504/100, 117; 424/93.3, 93.4, 93.43, 93.47, 93.5; 47/DIG. 9; 435/911

[56] References Cited

U.S. PATENT DOCUMENTS

| | | | |
|---|---|---|---|
| 4,294,037 | 10/1981 | Mosse | 47/59 |
| 4,327,181 | 4/1982 | Litchfield | 435/176 |
| 4,534,965 | 8/1985 | Brown | 424/93 |
| 4,551,165 | 11/1985 | Warner | 71/24 |
| 4,713,342 | 12/1987 | Chet | 435/254 |
| 4,996,157 | 2/1991 | Smith | 435/254 |
| 5,068,105 | 11/1991 | Lewis | 424/93 |
| 5,192,686 | 3/1993 | Ahmed | 435/254 |
| 5,244,658 | 9/1993 | Parke | 504/117 |
| 5,360,606 | 11/1994 | Parke | 424/93.47 |
| 5,403,583 | 4/1995 | Liu | 424/93.46 |
| 5,403,584 | 4/1995 | Crawford | 424/93.43 |
| 5,413,783 | 5/1995 | McLaughlin | 424/93.51 |
| 5,415,672 | 5/1995 | Fahey | 47/57.6 |

OTHER PUBLICATIONS

D.H. Marx, "The Influence of Ectotrophic Mycorrhizal Fungi on the Resistance of Pine Roots to Pathogenic Infections. I. Antagonism of Mycorrhizal Fungi to Root Pathogenic Fungi and Soil Bacteria", *Phytopathology* vol. 59, Feb. 1969, pp. 153–163.

W.A. Sinclair, D.P. Cowles, and S.M. Hee, "Fusarium Root Rot of Douglas–Fir Seedlings: Suppression by Soil Fumigation, Fertility Management, and Inoculation with Spores of the Fungal Synbiont *Laccaria laccata*", *Forest Science* vol. 21, Apr. 1975, pp. 390–399.

C.S. Rothrock and D. Gottlieb, "Role of Antibiosis in Antagonism of *Streptomyces Hygroscopicus* var. *geldanus* to *Rhizoctonia solani* in Soil," *Canadian Journal of Microbiology* vol. 30, 1984, pp. 1440–1447—published sufficiently before filing date such that the month is not an issue.

R. Tahvonen and H. Avikainen, "The Biological Control of Seed–Borne *Alternaria brassicicola* of Cruciferous Plants with a Powdery Preparation of Streptomyces sp.," *Journal of Agricultural Science in Finland* vol. 59, 1987, pp. 199–208—published sufficiently before filing date such that the month is not an issue.

L.C. Duchesne, R.L. Peterson, and B.E. Ellis (1988), "Interaction Between the Ectomycorrhizal Fungus *Paxillus involutus* and *Pinus resinosa* Induces Resistance to *Fusarium oxysporum*," *Canadian Journal of Botany* vol. 66, 1988, pp. 558–562—published sufficiently before filing date such that the month is not an issue.

E.N. Loopstra, C.G. Shaw, III, and R.C. Sidle, "Ectomycorrhizal Inoculation Fails to Improve Performance of Sitka Spruce Seedlings on Clear Cuts in Southeastern Alaska," *Western Journal of Applied Forestry* vol. 3, Apr. 1988, pp. 110–112.

R.L. Doudrick and N.A. Anderson, "Incompatibility Factors and Mating Competence of Two Laccaria spp. (Agricales) Associated with Black Spruce in Northern Minnesota," *Phytopathology* vol. 79, Jun. 1989, pp. 694–700.

M.H.R. Browning and R.D. Whitney, "Responses of Jack Pine and Black Spruce Seedlings to Inoculation with Selected Species of Ectomycorrhizal Fungi," *Canadian Journal of Forestry Research* vol. 21, 1991, pp. 701–706—published sufficiently before filing date such that the month is not an issue.

J.F. MacFall and F.A. Slack, "Effects of *Hebeloma arenosa* on Growth and Survival of Container–Grown Red Pine Seedlings (*Pinus resinosa*)," *Canadian Journal of Forestry Research* vol. 21, 1991, pp. 1459–1465—published sufficiently before filing date such that the month is not an issue.

P. Chakravarty and S.F. Hwang (1991), "Effect of An Ectomycorrhizal Fungus, *Laccaria laccata* on Fusarium Damping–off in *Pinus banksiana* Seedlings," *European Journal of Forest Pathology* vol. 21, 1991, pp. 97–106—published sufficiently before filing date such that the month is not an issue.

N.E. Strobel and W.A. Sinclair, "Influence of Temperature and Pathogen Aggressiveness on Biological Control of Fusarium Root Rot by *Laccara bicolor* in Douglas–Fir," *Phytopathology* vol. 81, Apr. 1991, pp. 415–420.

M.L. Lahdenpera, E. Simon and J. Uoti, "Mycostop–A Novel Biofungicide Based on Streptomyces Bacteria," in *Biotic Interactions and Soil–Borne Diseases*, 1991, A.B.R. Beemster et al., Eds., Elsevier, Amsterdam pp. 258–263—published sufficiently before filing date such that the month is not an issue.

M.H.R. Browning and R.D. Whitney, "Field Performance of Black Spruce and Jack Pine Inoculated with Selected Species of Ectomycorrhizal Fungi", *Canadian Journal of Forest Research* vol. 22, 1992, pp. 1974–1982—published sufficiently before filing date such that the month is not an issue.

(List continued on next page.)

Primary Examiner—John Pak
Attorney, Agent, or Firm—Schwegman, Lundberg, Woessner & Kluth, P.A.

[57] ABSTRACT

A novel method and composition is provided to control Fusarium root rot and damping off on conifer seedlings. When certain bacteria and an ectomycorrhizal fungus are placed in contact with the conifer seed or seedling, the combination reduces or eliminates disease symptoms caused by several Fusarium species.

5 Claims, No Drawings

OTHER PUBLICATIONS

N.S. El–Abyad, M.A. El–Sayed, A.–R. El–Shanshoury and N.H. El–Batanouny, "Inhibitory Effects of UV Mutants of *Streptomyces corchorusii* and *Streptomyces spiroverticillatus* on Bean and Banana Wilt Pathogens," *Canadian Journal of Botany*, vol. 71, 1993, pp. 1080–1086—published sufficiently before filing date such that the month is not an issue.

G. Gay, R. Marmeisse, P. Fouillet, M. Bouletreau and J.C. Debaud, "Genotype/Nutrition Interactions in the Ectomycorrhizal Fungus *Hebeloma cylindrosporun* Romagnesi," *New Phytologist* vol. 123, 1993, pp. 335–343—published sufficiently before filing date such that the month is not an issue.

C.M. Ocamb, "Microbes Isolated from White Pine Nursery Soil to Suppress Pathogenic Fusarium Species," *Phytopathology* vol. 84, Oct. 1994, pp. 1137–1138.

R.G. Linderman, "Role of VAM Fungi in Biocontrol," in *Mycorrhizae and Plant Health*, 1994, F.L. Pfleger and R.G. Linderman, Eds., pp. 1–25—published sufficiently before filing date such that the month is not an issue.

L.C. Duchesne, "Role of Ectomycorrhizal Fungi in Biocontrol," in *Mycorrhizae and Plant Health*, 1994, F.L. Pfleger and R.G. Linderman, Eds., pp. 27–45—published sufficiently before filing date such that the month is not an issue.

M.A. Castellano, "Current Status of Out–Planting Studies Using Ectomycorrhiza–Inoculated Forest Trees", in *Mycorrhizae and Plant Health*, 1994, F.L. Pfleger and R.G. Linderman, Eds., pp. 261–281—published sufficiently before filing date such that the month is not an issue.

C.M. Ocamb and J. Juzwik, "Fusarium Species Associated with Rhizosphere Soil and Diseased Roots of Eastern White Pine Seedlings and Associated Nursery Soil," *Canadian Journal of Plant Pathology* vol. 17, 1995, pp. 325–330—published sufficiently before filing date such that the month is not an issue.

K.A. El–Tarabily, M.L. Sykes, I.D. Kurtboke, G.E. St. J. Hardy, A.M. Barbosa and R.F.H. Dekker, "The Combined Synergistic Effects of a Cellulase–producing *Micromonospora carbonacea* and An Antibiotic–producing *Streptomyces violascens* on the Suppression of Root–rot Disease of *Banksia grandis* Caused by *Phytophthora cinnamomi*," talk at a meeting of the American Phytopathological Society, Jul. 30, 1996, Indianapolis, Indiana.

Chakravarty, P. et al. *Can J For Res* 20(9):1283–1288 (1990).

Kope, H et al. *Can J Bot* 68(6):1254–1259 (1990).

Sinclair, W. A. et al. *For Sci* 28(2):199–201 (1982).

CABA Abstract 90:138243 (1990).

CROPU Abstract 94:85082 (1993).

BIOSIS Abstract 83:163467 (1982).

BIOSIS Abstract 90:42447 (1990).

BIOSIS Abstract 96:129625 (1995).

BIOSIS Abstract 90:521780 (1990).

Hwang, S.F. et al. "The effect of two ectomycorrhizal fungi, *Paxillus involutus* and *Suillus tomentosus*, and of *Bacillus subtilis* on Fusarium damping–off in Jack Pine Seedlings," Phytoprotection, vol. 76, No. 2, 1995, pp. 57–66.

BIOLOGICAL CONTROL OF PLANT DISEASE ON ROOTS OF CONIFER SEEDLINGS

The U.S. Government has a paid-up license in this invention and the right in limited circumstances to require the patent owner to license others on reasonable terms as provided for by the terms of Grant Nos.: USDA-FS 24-42-TN-031114; USDA-FS 152103; and USDA-FAS-RSED SF08 awarded by the United States Department of Agriculture.

BACKGROUND OF THE INVENTION

The production of conifers from seed is greatly affected by Fusarium root rot, in which seedling roots are destroyed by infection with the soil-inhabiting fungus Fusarium. That disease, which can be caused by *Fusarium oxysporum, F. oxysporum* var. *redolens, F. proliferatum,* or *F. solani*, kills 20–90% of conifer seedlings grown in the Lake States region each year, and reduces the vigor and growth of infected seedlings which are not killed, as discussed in the 1983, 1985, and 1986 editions of Prey, et al., Forest Pest Conditions in Wisconsin, Annual report. Department of Natural resources, Div. of Resource Management, Bureau of Forestry, Madison, Wis. Fusarium can also cause damping-off disease, in which the stem of the seedling near the soil line is destroyed.

Current measures for controlling soil Fusarium spp. include soil fumigation with methyl bromide-chloropicrin in bareroot nurseries, and frequent fungicide applications to greenhouse-grown plants. These measures are often ineffective in controlling seedling Fusarium diseases because Fusarium spp. is often present in the seed. Also, methyl bromide-chloropicrin soil fumigation may not be allowed after the year 2000 because its use is viewed as an environmental hazard. R. S. Smith and S. W. Fraedrich (1993), "Back to the future—pest management without methyl bromide", Tree Planters' Notes 44:87–90. Thus, alternatives are needed for controlling Fusarium diseases in tree nurseries.

The use of biological control agents (living microorganisms used to control pests) is gaining recognition as an alternative disease control. The effective use of bacteria, actinomycetes, and fungi as agents for biological control of soil-borne plant disease has been demonstrated in several instances. Among the useful biological control bacteria are *Bacillus megetarium*, which controls *Rhizoctonia solani* on soybean, as disclosed in U.S. Pat. No. 5,403,583, and a mixture of combinations of three Pseudomonas spp. a Corynebacterium sp., and two Bacillus spp., which controls Aphanomyces root rot of peas, as disclosed in U.S. Pat. No. 5,244,658.

Actinomycetes are bacteria with fungus-like growth characteristics. Several isolates of the actinomycete Streptomyces have proved effective as biological control agents against soil-borne plant pathogens. A commercial product, Mycostop® biofungicide, contains an isolate of *S. griseoviridis* as its active ingredient. That product is effective as a seed and soil treatment against seed rots, root and stem rots, and wilt diseases of various ornamental plants, caused by Fusarium spp. and other fungi. M-L. Lahdenper ä, et al. (1991), "Mycostop—A novel biofungicide based on Streptomyces bacteria", pp.258–263 in *Biotic Interactions and Soil-Borne Diseases*, A. B. R. Beemster, et al., eds., Elsevier, Amsterdam. The Mycostop® Biofungicide Directions for Use (Kemira Biotech, Helsinki, Finland) recommends Mycostop® for use on pine and other conifers.

Another Streptomyces sp. isolate, designated WYEC 108, disclosed in U.S. Pat. No. 5,403,584, is effective as a seed treatment against damping-off of chickpea caused by Pythium spp. That patent also described some inhibitory activity against Fusarium growing in agar-solidified growth media in petri plates.

Other Streptomycetes used for biological control include mutants of *S. corchorusii* and *S. spirovirticillatus*, effective against Fusarium wilt of French bean and the organism which causes bacterial wilt of banana (*Pseudomonas solanacearum*), described in El-Abyad, et al. (1993), "Inhibitory effects of UV mutants of *Streptomyces corchorusii* and *Streptomyces spiroverticillatus* on bean and banana wilt pathogens", Can. J. Bot. 71:1080–1086, and *S. hygroscopicus* var. *geldanus*, which controlled Rhizoctonia root rot of pea, caused by *R. solani*, described in C. S. Rothrock and D. Gottlieb (1984), "Role of antibiosis in antagonism of *Streptomyces hygroscopicus* var. *geldanus* to *Rhizoctonia solani* in soil", Can. J. Microbiol. 30:1440–1447.

Various fungi have been utilized as biological control agents to control fungal plant pathogens. Two yeasts, *Pichia guilliermondii* and *Hanseniasporum uvarum*, are effective in controlling preharvest and postharvest development of several pathogens on numerous commodities, as disclosed in U.S. Pat. No. 5,413,783. Several isolates of Trichoderma spp. have also been employed to control soil-borne diseases, as disclosed in U.S. Pat. Nos. 4,996,157 and 5,192,686, including Fusarium spp. on cotton, disclosed in U.S. Pat. No. 4,713,342.

Mycorrhizae are fungi which infect and form mutualistic relationships with plant roots. These fungi can improve plant growth by increasing the plant's assimilation of nutrients, especially phosphorus, which are sparingly soluble in the soil. Mycorrhizal infection will often make the plant roots more resistant to various soil-borne fungal pathogens. There are two major types of mycorrhizae: vesicular-arbuscular (VA) mycorrhizae, which infect most cultivated plants and produce specialized structures (vesicles or arbuscules) in the root cells, and ectomycorrhizae, which infect many forest trees such as pines and other conifers. Compositions and methods have been developed to help efforts to artificially inoculate plants with mycorrhizae. See, for example, U.S. Pat. Nos. 4,551,165 and 5,178,642. Also see a review of these efforts in M. A. Castellano (1994), "Current status of outplanting studies using ectomycorrhizae-inoculated forest trees", pp. 261–281 in *Mycorrhizae and Plant Health*, F. L. Pfleger and R. G. Linderman, eds., APS Press, St. Paul.

Ectomycorrhizal fungi are generally capable of infecting many species of plants. The ectomycorrhizal fungus which has been the most extensively investigated, Pitholithus sp., has been used to infect several species of the following woody plants: pine (Pinus), oak (Quercus), acacia (Acacia), and eucalyptus (Eucalyptus). Id. Additionally, many genera of ectomycorrhizal fungi, including Hebeloma and Laccaria, have been shown to be capable of infecting herbacious plants such as corn and wheat, as disclosed in U.S. Pat. No. 5,178,642. Thus, ectomycorrhizal fungi can be generally considered to be somewhat nonspecific in the plants they infect.

Both VA mycorrhizae and ectomycorrhizae have been utilized as biological control agents, with limited success. That work is reviewed in R. G. Linderman (1994), "Role of VAM fungi in biocontrol", pp. 1–25 Id., and L. C. Duchesne, "Role of ectomycorrhizal fungi in biocontrol", pp. 27–45 Id.

Ectomycorrhizae have shown some promise in controlling soil-borne diseases on conifer seedlings, but the protection to date has been unreliable due to the extreme variability of results. For example, Laccaria spp. exhibited limited control against Fusarium root rot and damping off on Douglas fir (described in N. E. Strobel and W. A. Sinclair (1991), "Influence of temperature and pathogen aggressiveness on biological control of fusarium root rot by Laccaria bicolor in douglas-fir", Phytopathol. 81:415–420) and pine (in P. Chakravarty and S. F. Hwang (1991), "Effect of an ectomycorrhizal fungus, *Laccaria laccata*, on Fusarium damping-off in *Pinus banksiana* seedlings", Eur. J. For. Path. 21:97–106, and *Paxillus involutus* increased resistance of pine seedlings by 47% to Fusarium root diseases, as described in L. C. Duchesne, et al. (1988), "Interaction between the ectomycorrhizal fungus *Paxillus involutus* and *Pinus resinosa* induces resistance to *Fusarium oxysporum*", Can. J. Bot. 66:558–562. Because of the limited and conditional control exhibited in these studies, the authors have expressed pessimism that they could be used effectively without further extensive research. See N. E. Strobel and W. A. Sinclair, supra, and L. C. Duchesne (1994), supra.

The present invention addresses a long felt need to provide an alternative to chemical control methods by utilizing a strategy employing novel ectomycorrhizae and Streptomyces isolates alone and in combination to effectively control conifer seedling diseases caused by Fusarium.

FIELD OF THE INVENTION

The present invention relates to the use of ectomycorrhizal fungi in combination with soil bacteria to inhibit disease caused by Fusarium spp. and to establish ectomycorrhizal infections.

SUMMARY OF THE INVENTION

In accordance with the present invention, conifer seeds or nascent seedlings are contacted with a composition comprising a mixture of two genera of microorganisms, namely, a biologically pure culture of an ectomycorrhizal fungus capable of colonizing the roots of a conifer, and a biologically pure culture of a bacterial control agent inhibitory to the growth of Fusarium spp. This composition may be applied to seeds prior to planting, or to young seedlings undergoing transplantation. The invention thus provides a method for reducing the incidence of Fusarium infection in conifer seedlings grown from conifer seeds. This is an important advance in the art since Fusarium infestations in nurseries can obliterate conifer stocks, and reduce the survival of more mature seedlings which must be thinned and transplanted.

In an alternative method, conifer seeds are first coated with a culture of the bacterial biological control agent. The residue is allowed to dry to form a protective coating, and upon planting, the region of planting medium surrounding the seed is impregnated with a culture of the ectomycorrhizal fungus. A further embodiment involves first coating the seed with the biological control agent, and then later, after the seed has germinated seedling has emerged, further treating the nascent root with a culture of ectomycorrhizae upon transplantation, or adding it to the plant-growth medium in sufficient quantity to saturate the region surrounding the rhizosphere. Since the principal manifestations of Fusarium infection are the formation of root rot and damping off of plant stems, the methods of the invention result in reduction in the incidence of root rot and damping off.

The present invention can also be adapted to providing a preformed plant-growth media, which comprises conventional soil and processed support material such as vermiculite, perlite, sand, and the like. Preferably the final mix is sterilized or pasteurized by heat or steam. Cultures of the combination of an ectomycorrhizal fungus capable of colonizing conifer roots, and a biologically pure culture of a bacterial control agent inhibitory to Fusarium spp. are then blended with the conventional medium to obtain a media ready for conifer seed planting. This preformed medium is especially efficacious for large nurseries where large numbers of seedlings are managed, and labor factors are critical.

In the methods and compositions of the present invention, a preferred ectomycorrhizal fungus is *Hebeloma arenosa* NRRL 21841, and preferred bacterial control agents are *Methylobacterium mesophilicum*, NRRL B-21842, the actinomycetes *Streptomyces lavendulae* NRRL 21838, *S. rochei* subsp. *rochei* NRRL 21839, and *S. violaceusniger* subsp. *violaceusniger* NRRL 28140, and a mixture of biologically pure cultures of the bacteria *Rhodococcus erythropolis*, *Kocuria varians*, and *Pseudomonas diminuta*, NRRL B-21843. All cultures or mixtures identified by "NRRL" number herein identify cultures or mixtures of cultures prepared or isolated as described below, which were deposited with the National Center for Agricultural Utilization Research, 1815 North University Street, Peoria, Ill. 61604, in accordance with the terms of the Budapest Treaty.

DETAILED DESCRIPTION OF THE INVENTION

The present invention relates to the utilization of a newly isolated ectomycorrhizal fungus and combinations of that fungus with newly isolated bacteria on conifer seedlings to reduce the incidence and severity of root rot and damping off caused by Fusarium species, and efficiently establish a beneficial ectomycorrhizal relationship on those seedlings. The newly isolated fungus, a Hebeloma, is unusual in its superior ability to reduce the effects of Fusarium root rot and establish an ectomycorrhizal relationship on conifer seedlings alone in soil and in combination with the newly isolated bacteria. These bacteria are also superior to other bacteria in the prior art in their ability to reduce the effects of Fusarium root rot when applied alone or in combination with Hebeloma. These bacteria also help the Hebeloma to establish an ectomycorrhizal relationship with conifer seedlings.

A "biological control agent" or BCA is herein defined as a microorganism which can reduce the effects of plant disease when applied in the environs of the plant disease—causing organism.

The utilization of a combination of two different genera of microorganisms for biological control is novel, and the combination disclosed in this invention satisfies a need for alternatives to chemical plant disease control, as by methyl bromide-chloropicrin.

The nonmycorrhizal bacteria, which are also referred herein as "bacterial control agents" or nonmycorrhizal BCAs, are *Streptomyces rochei* subsp. *rochei* NRRL 21841, *Streptomyces violaceusniger* subsp. *violaceusniger* NRRL 21840, *Streptomyces lavendulae* NRRL 21838, *Methylobacterium mesophilicum* NRRL B-21842, and mixtures of biologically pure cultures of *Rhodococcus erythropolis*, *Kocuria varians*, and *Pseudomonas diminuta*, NRRL B-21843. These are the first bacterial control agents known for these species. They are highly effective bacterial control agents when used alone and in combination with *Hebeloma arenosa* NRRL 21841.

The term "biologically pure culture" is used herein to refer to cultures of organisms which have subcultured to species homogeneity by mass transfer.

Isolation of the ectomycorrhizal fungi

Although ectomycorrhizal fungi have not been shown to be effective BCAs in the past, isolates of Hebeloma and Laccaria were obtained from conifer nurseries having an unusually high incidence of Fusarium root rot. Species derived from healthy plants in such an environment may be more robust in colonizing conifer roots then in less infested environments. The Hebeloma isolated is unusually effective in its ability to colonize roots in the presence of Fusarium and in its ability to protect conifer seedlings from Fusarium root rot.

Ectomycorrhizal fungi may be isolated from the roots of trees or, preferably, from the fruiting body of the fungus, such as a mushroom, which arise from the soil adjacent to the trees infected with the fungus. The ectomycorrhizal fungus *Hebeloma arenosa* NRRL 21841 was isolated from a mushroom found in a conifer nursery, specifically the F. G. Wilson State Forest Nursery in Boscobel, Wis. Another ectomycorrhizal fungus, *Laccaria bicolor,* was isolated from a mushroom growing in General Andrews Nursery, Willow River, Minn. *Laccaria bicolor* is often treated as the same species as *Laccaria laccata*. See, for example N. E. Strobel and W. A. Sinclair (1991) supra. Laccaria, but not Hebeloma has been previously studied as a potential BCA, exhibiting limited control of Fusarium root rot. These two fungi were isolated from single-spore colonies by the method described in R. L. Doudrick and N. A. Anderson (1989), "Incompatibility factors and mating competence of two Laccaria spp. (Agaricales) associated with black spruce in northern Minnesota", Phytopathology 79:694–700.

These ectomycorrhizal fungi may be cultured in a culture medium under conditions suitable for rapid growth and retention of the ability to form an ectomycorrhizal relationship with the conifer root and ability to inhibit plant disease. The preferred medium is Melin-Norkrans' nutrient solution, which is described in D. H. Marx (1969), "The influence of ectotrophic mycorrhizal fungi on the resistance of pine roots to pathogenic infections. I. Antagonism of mycorrhizal fungi to root pathogenic fungi and soil bacteria", Phytopathology 59:153–163. Isolates may be stored on agar slants of Modified Melin-Norkrans' medium as described in D. H. Marx, supra.

Preparation and use of root rotting fungi

Root rotting isolates of Fusarium are the preferred pathogens for evaluation of the BCAs. Although other organisms causing root rot on conifers (such as Cylindrocladium) could be used, Fusarium is preferred because it causes the most incidences of root rot in conifer nurseries, it is present essentially everywhere conifers are grown, and it is easy to grow, store, and manipulate.

Several species of Fusarium will cause root rot and can generally be treated interchangeably. Preferred for this invention are pathogenic isolates of four Fusarium species, *F. oxysporum, F. oxysporum* var. *redolens, F. proliferatum,* & *F. solani*, which are the most frequent species causing Fusarium root rot of conifers. See C. M. Ocamb and J. Juzwik (1995), "Fusarium species associated with rhizosphere soil and diseased roots of eastern white pine seedlings and associated nursery soil", Can. J. Plant Pathol. 17:325–330. Fusarium can be stored and grown in a variety of ways. See pp. 25–27 and 61–75 in O. D. Dhingra and J. B. Sinclair (1995), *Basic Plant Pathology Methods*, CRC Press, Boca Raton. To assure the maintenance of pathogenicity and morphology, the following methods are preferred. Each isolate is grown from a single spore and stored on silica gel at 5° C. Fusarium isolates are preferably grown from silica gel crystals on carnation leaf agar (CLA) (see p. 347 in O. D. Dhingra and J. B. Sinclair, supra).

For petri dish overlay studies, the Fusarium may be overlaid onto growing cultures of BCA candidates, then incubated so that BCA candidates which inhibit the growth of the Fusarium in the overlay will cause a zone of inhibition around the candidate organism. More effective BCA candidates will show a larger zone of inhibition than less effective candidates. The following method, which is similar to that summarized in C. M. Ocamb (1994), "Microbes isolated from white pine nursery soil to suppress pathogenic Fusarium species", Phytopathology 84:1137–1138, is the preferred overlay method because it is simple to carry out and each BCA candidate which inhibits Fusarium growth causes a reproducible zone of inhibition.

The BCA candidates, either in a biologically pure culture or in a diluted matrix (such as soil) which contains many organisms, may be grown for about 72 hours in agar-solidified medium containing various mineral salts (see p. 390 in O. D. Dhingra and J. B. Sinclair, supra). A carbon source consisting of cellulose, pectin, or chitin is added. The entire Fusarium culture may be homogenized, diluted into molten, cooled Czepak-Dox agar (see p. 349–350 in O. D. Dhingra and J. B. Sinclair, supra), and overlaid onto the growing culture of the BCA candidate. BCAs will be selected having the greatest inhibition of Fusarium growth or largest inhibition zone.

For testing BCAs, the Fusarium is first inoculated into growing medium and grown into a dense biologically pure culture. This culture may be conveniently mixed with the plant-growing medium and reliably cause root rot on a large proportion of conifer seedlings sown therein. In a preferred method, a 5-mm agar plug is taken from 10- to 14-day old CLA cultures and transferred to sterile cornmeal-sand medium (97 g sand, 3 g cornmeal, 40 ml distilled water) in 150 ml glass jars. The cornmeal-sand cultures are incubated 4–6 wk at 25 C. The cultures are then dried thoroughly in a laminar flow hood. Dried inoculum is then thoroughly mixed into the plant-growing medium to give a final concentration of approximately 15,000–25,000 colony-forming units per gram of oven-dried soil.

Isolation and use of Nonmycorrhizal BCAs

The nonmycorrhizal BCAs (bacterial agents) are grown using known culture methods. A suitable medium will allow the bacteria to achieve rapid growth and retain the ability to inhibit plant disease. BCA candidates are screened for the ability to enhance the fungus' ability to form an ectomycorrhizal relationship. There are several commercially available media which are suitable, with the preferred media being King's B or oatmeal broth. See for example R. A. Lelliott and D. E. Stead (1987), *Methods for the Diagnosis of Bacterial Diseases of Plants*, Blackwell Scientific Publications, Oxford.

Although BCAs which are effective against root rot might be found in any soil, they may be more abundant in the rhizosphere (the area of soil around plant roots) than in areas of soil which do not contain plant roots. U.S. Pat. No. 5,403,584 discloses greater numbers of potential BCA actinomycetes isolated from a rhizosphere than from non-rhizosphere soil. Therefore, the BCAs of the present invention are isolated from rhizosphere soil.

U.S. Pat. No. 5,360,606 discloses the isolation of BCAs from the rhizosphere of peas which are effective in controlling root rot of peas. In the present invention, however, BCAs effective against conifer root rot are derived from white pine (since it is desirable to obtain a BCA effective against conifer diseases). BCAs isolated from corn rhizosphere, *Methylobacterium mesophilicum* NRRL B-21842, and a mixture of biologically pure bacteria *Rhodococcus erythropolis, Kocuria varians*, and *Pseudomonas diminuta*, NRRL B-21843 were surprisingly effective. Another aspect of the identification of these BCAs is that they were not isolated from corn rhizospheres using an overlay method. Rather, they were found in association with a Fusarium isolated from corn roots. In overlay tests, however, these BCAs were found to strongly inhibit Fusarium.

When isolating BCAs from rhizosphere soil using the plate dilution method described supra, the soil may be diluted in any of a number of media which will allow the BCAs to grow. However, cellulose, pectin, and chitin media is preferred because they select for specifically adapted microorganisms, ones believed to compete well in the rhizosphere. Collected soil may be diluted 2000-fold in molten but cooled cellulose, pectin, or chitin media, poured into petri dishes and incubated approximately 72 hours. A Fusarium overlay may be added, and the petri dishes incubated. The microorganisms which are selected for further study as BCA candidates will be those at the center of zones of inhibition greater than 1 mm in diameter. In one study, 586 BCA candidates were isolated by this method.

These BCA candidates may be tested directly in soil with target conifer seedlings, but preferably, candidates are retested by a petri dish—Fusarium overlay method similar to that used with the soil dilutions. The candidates are transferred onto a petri dish containing Czepak-Dox agar, where they grow out in biologically pure culture. The overlay comprises a mixture of Fusarium, preferably a mixture of isolates of four Fusarium identified as root rot-causing isolates of *F. oxysporum, F. oxysporum* var. *redolens, F. proliferatum*, & *F. solani*. In a continuation of the study referred to above, 61 BCA candidates, out of the originally selected 586, showed strong ability to prevent the combined four species of Fusarium from growing on petri dishes.

BCA candidates which have survived at least one round of selection using Fusarium mixtures overlaid are further tested for their ability to control Fusarium root rot in conifer seedlings in a second step selection. It is believed the BCA contacts the seed or seedling parts which are below the soil surface, such as roots of seedling transplants, or the seed itself. In a preferred embodiment, the BCA is inoculated into sterile medium, preferably oatmeal broth, in containers suitable for culturing microorganisms, which are maintained in aerobic growth phase. Conifer seeds are stratified (a cold or chemical treatment required for many conifer seed varieties to germinate). They are then contacted with the liquid culture of the appropriate BCA for time sufficient to bind the BCA to the seed, as by immersion or spraying. "Immerse" is herein defined as, to thoroughly wet. A very brief immersion, long enough to allow the seed surface to become completely wet, is sufficient; however the seed may be kept covered with the liquid culture for as long as six hours at room temperature and 24 hours at 4 C without deleterious effect on the seed. The preferred time is 60 min.

The seeds may then be dried by any method which would retain the viability of the seed and a sufficient amount of the BCA to be effective. The seeds may be air-dried by any convenient method, for example by spreading the wet seeds on a screen and blowing air through the screen. The preferred embodiments of the seed soaking method have yielded approximately $10^3$ to $10^5$ colony-forming units per seed.

The BCAs may be used in soil or an artificial planting mix such as those used by professional growers of conifers. These planting mixes may contain peat, bark, perlite, vermiculite, sand, compost, or other ingredients well known in the art. The BCAs may also be used with container-grown seedlings or seedlings grown in the ground, and seedlings grown outdoors, in greenhouses, in shadehouses, or in growth chambers.

When testing candidate BCAs, the plant growing medium can be naturally infested with a plant disease, or the causal agent of the plant disease can be added artificially. Artificial addition of a mixture of the 4 pathogenic Fusarium species previously mentioned is preferred because one can then discern ECAs which are effective against several species of Fusarium. The pathogen is added to the plant-growing medium in a way to get consistent, reliable root rot symptoms in seedlings grown in the medium from seed or added by transplanting growing seedlings into the medium. Each of the four Fusarium isolates, prepared in sterile cornmeal-sand medium as disclosed above, is added to the plant-growing medium at a rate of about 0.0025 to 0.010 g/cc plant growing medium. The medium may be evaluated for propagule numbers of each Fusarium species by conducting a dilution series of the soil, by standard methods. See, for example p. 86 in O. D. Dhingra and J. B. Sinclair, supra.

When growing seedlings in containers, any container and plant-growing medium where an added BCA will provide control of root rot may be used. For example, pine cell cone-tainers (Stuewe & Sons, Corvallis, Oreg.), 17 cm long and 24 mm in diameter, are plugged with 5 cc of non-infested plant-growing medium then, if a pathogen is desired, a quantity of Fusarium-infested growing medium is added via a sterile PVC tube (18 mm OD, 12 mm ID) attached to a sterile 65 mm polypropylene funnel. The pine cells are then almost filled with non-infested soil. The conifer is sown, in duplicate, either as seedling transplants, or preferably as stratified seed. If the seed or seedlings have not been previously been treated with a BCA, for example by using the seed coating method described above, the BCA is added in a manner which will provide sufficient contact with the seed or seedling to provide control of Fusarium root rot. Examples of alternative methods of applying effective amounts of BCAs in soil include application as a culture or on a carrier to the soil at planting near the seed or seedling, or adding the BCA as a liquid culture or in a solid or liquid carrier to the soil after planting. U.S. Pat. Nos. 5,415,672; 5,403,58; 5,403,583; 4,996,157; 4,534,965; and 4,713,432 disclose suitable methods.

An ectomycorrhizal fungus may be contacted with the seed or seedling by any means known in the art, including using a plant-growing mix which contains the fungus prepared before planting, as was described as a "Ball mix" in J. S. MacFall and S. A. Slack (1991), "Effects of *Hebeloma arenosa* on growth and survival of container-grown red pine seedlings (*Pinus resinosa*)", Can. J. For. Res. 21:1459–1465. In the preferred embodiment, *Hebeloma arenosa* NRRL 21841 is grown in modified Melin-Norkrans' nutrient solution, as described in Marx, supra. Prior to application to the plant-growing medium, the cultures are leached with sterile distilled water to wash away nutrients. Sterile glass beads may be added to break up the mycelial pieces with manual agitation. The fungus is added to the soil by adding some of this preparation to the plant-growing medium at the time of planting.

It is important to note that these organisms are controlled participants in an environment in which microecological balance in the numbers of organisms is effected naturally as the seedlings develop. Therefore, the ratios and numbers of the respective ectomycorrhizae and BCA do not conform to set ranges and may be arbitrarily selected so long as a sufficient inoculum is used to ensure a generally uniform distribution of organisms in the rhizosphere. Generally, a one ml aliquot of this fungal preparation will contain about 250 to 550 colony forming units. In the preferred embodiment, the ratio of bacterial agent to Hebeloma, in colony forming units, is between about 19 and 37.

Since all ectomycorrhizal fungi will infect a number of plant species, *Hebeloma arenosa* NRRL 21841 will be beneficial for any conifer. Hebeloma has been utilized as an ectomycorrhizae on pine, Sitka spruce, (E. M. Loopstra, et al., 1988), black spruce, (M. H. R. Browning and R. D. Whitney, 1992), and angiosperm species, (G. Gay, et al., 1993).

Containers in with the treated seed or seedling is planted may be placed outdoors, in a greenhouse, in a shadehouse, or in a growth chamber as desired, where they may be maintained following good horticultural practice.

The BCA and ectomycorrhizal fungus may be added together or separately, in either order. It is important that they be in proximity to the rhizosphere of the emerging root.

Fusarium root rot symptoms can develop within 4 months after sowing, and any time thereafter seedlings may be evaluated for the presence of disease. The preferred method involves removal of seedlings from the containers. Excess soil is then washed off the roots. Severity of root rot is then assessed for each seedling. Root rot is manifested as brown root tissue which is soft or macerated. Root rot is assessed by rating the roots on a 1 to 5 scale: 1=apparently healthy; 2=over 50% length of one lateral root is exhibiting rot; 3=lower ⅓ of tap root is symptomatic or greater than 50% of two or more lateral roots is necrotic; 4=lower ⅔ of tap root is rotted (with or without lateral root injury); 5=upper ⅓ of tap root is rotted or entire root system is affected. If roots exhibit rot, then small segments of tissues are excised from the edge of the necrotic areas, disinfested in 0.5% NaOCl for 1 minute, then embedded into solidified pentachloronitrobenzene-peptone agar supplemented with aureomycin (Nash medium). Cultures on Nash medium are incubated up to 21 days at 24 C with indirect lighting. Confirmation of Fusarium species may be done by transferring colonies to potato dextrose agar and CLA for classification according to methods known to the art. See for example O. D. Dhingra and J. B. Sinclair, supra, at p. 25.

EXAMPLES

Example 1

Evaluation of BCA candidates for effectiveness in controlling Fusarium root rot

The effectiveness of 61 BCA candidates, isolated by the Fusarium overlay method, was determined using cone-tainers and a field soil. A loamy sand field soil with an organic content of 1–2% and average bulk density of 1.20 g/cm$^3$, was collected from a white pine field at F. G. Wilson State Forest Nursery in Boscobel, Wis. The soil was pasteurized by enclosing it in plastic shoe boxes, and steaming at 12 psi for 60 min on each of two consecutive days. The cone-tainers were placed in a greenhouse where the seeds germinated and the seedlings were grown up. Starting at four weeks, the seedlings were fertilized weekly with a 20-7-19 liquid fertilizer, at 150 ppm. About six weeks after sowing, the seedlings were thinned to a single seedling per cone-tainer. The study was conducted twice. In the first test, the seedlings were evaluated for root rot after four months; in the second test, seedlings were evaluated after six months. The commercial *Streptomyces griseoviridis* preparation Mycostop® was included in these evaluations. In these studies, the commercial product Mycostop® was added as a soil drench every four weeks, unlike the other BCAs tested, which were only applied as a seed coat at planting. Results of studies using a one-time seed coating at planting showed Mycostop® to be ineffective in reducing Fusarium root rot on conifer seedlings. Table 1 summarizes the averaged results of both evaluations for the bacterial agents claimed herein (in bold) along with other, representative, BCA candidates. The isolates which were the most effective in reducing the incidence and/or severity of root rot were: BCT 19b =*Streptomyces rochei* subsp. *rochei* NRRL 21839, deposited Oct. 10, 1997; BCT 5a =*Streptomyces violaceusniger* subsp. *violaceusniger* NRRL 21840, deposited Oct. 10, 1997; BCB 176=*Streptomyces lavendulae* NRRL 21838, deposited Dec. 12, 1997; and BC 19=*Methyobacterium mesophilicum*, deposited Oct. 10, 1997; and BC 20=a mixture of biologically pure cultures of the bacteria *Rhodococcus erythropolis, Kocuria varians,* and *Pseudomonas diminuta*, NRRL B-21843, deposited Oct. 10, 1997.

TABLE 1

Greenhouse evaluation of rhizosphere BCAs for Fusarium root rot using 4 pathogenic Fusarium isolates. The alarmed BCAs are in bold type.

| BCA candidate | Mean Root Rot Severity | % Healthy Seedlings |
| --- | --- | --- |
| BCT 3b | 1.4 | 59 |
| BCT 5a | 1.5 | 67 |
| BCT 5b | 1.9 | 39 |
| BCT 6b | 2.3 | 29 |
| BCT 8a | 2.3 | 39 |
| BCT 8b | 2.3 | 21 |
| BCT 11a | 1.4 | 71 |
| BCT 11b | 1.6 | 58 |
| BCT 12a | 2.0 | 44 |
| BCT 12b | 2.4 | 20 |
| BCT 19b | 1.3 | 83 |
| BCT 48 | 2.4 | 35 |
| BCT 62 | 2.1 | 29 |
| BCT 124 | 1.9 | 40 |
| BCT 205 | 2.2 | 34 |
| BCB 41 | 2.1 | 38 |
| BCB 70 | 1.6 | 60 |
| BCB 151 | 1.9 | 48 |
| BCB 152 | 1.6 | 60 |
| BCB 172 | 1.4 | 64 |
| BCB 175 | 1.4 | 72 |
| BCB 176 | 1.1 | 90 |
| BCB 191a | 2.6 | 24 |
| BCB 226 | 1.8 | 49 |
| BCB 229 | 1.6 | 55 |
| BCB 282 | 1.7 | 58 |
| BCB 284a | 1.9 | 48 |
| BCB 284b | 1.7 | 45 |
| BCB 285 | 1.9 | 33 |
| BCB 311 | 1.4 | 76 |
| BCB 314 | 2.0 | 34 |
| Strept 15 | 1.2 | 87 |
| Strept 32 | 1.8 | 39 |
| Strept 93 | 1.6 | 71 |
| BC 18 | 2.0 | 25 |
| BC 19 | 1.5 | 57 |
| BC 20 | 1.0 | 97 |
| BC 23 | 2.6 | 15 |
| Mycostop | 1.5 | 65 |
| infested control | 2.2 | 24 |

Example 2

Example 2 was conducted to evaluate two ectomycorrhizal fungi for effectiveness as BCAs and in establishing mycorrhizal infection on eastern white pine growing in the field soil used in Example 1. The pasteurized soil was used in the preferred method where BCA-coated seeds are planted in cone-tainers. In some cases the four isolates of Fusarium were added. To infect the planted seed with an ectomycorrhizal fungus, one ml of the fungus, which had been grown in modified Melin-Norkrans' nutrient solution, was added to the soil. The seeds were then covered with soil, then further covered with a layer of perlite.

The two isolates of ectomycorrhizal fungi used here were *Hebeloma arenosa* NRRL 21841, deposited Sep. 29, 1997, and Laccaria bicolor. The cone-tainers were placed in a growth chamber for 16 weeks where the seeds germinated and grew. The soil was removed and the roots evaluated. The percentage of the root system with mycorrhizal roots was also determined by visually determining the number of lateral roots and the number of those roots colonized by the fungus. The results are in Table 2.

These results show that Hebeloma is much more effective than Laccaria in establishing a mycorrhizal relationship. The Hebeloma-treated seedlings had a 40% greater proportion of ectomycorrhizal infection in the absence of Fusarium than the Laccaria-treated seedlings. In the presence of Fusarium, the Hebeloma was also able to maintain a mycorrhizal relationship when subjected to pathogenic Fusarium spp., whereas Laccaria was not.

Most importantly, Table 2 shows that Hebeloma was more successful than Laccaria in controlling Fusarium root rot, since the Hebeloma, Fusarium combination treatments had a 385% greater number of healthy seedlings and a 68% lower mean root rot rating than Laccaria, Fusarium combination treatments. In general, any ectomycorrhizae having 30- root colonizing incidence greater than Laccaria and a 50% lower root rot rating than Laccaria will have efficacy as a separate, independent seedling root treatment. Thus, Laccaria, the only ectomycorrhizae heretofore described as a BCA for controlling Fusarium root rot, was inferior to *Hebeloma arenosa* NRRL 21841 and not acceptable for that purpose.

The plant-growing medium used was Fafard #2, which is a medium commonly used by commercial growers to grow conifer seedlings. Fafard #2 mix is composed of 70% Canadian peat, 20% perlite, 10% #3 vermiculite, and 5 lb dolomite/cubic yard. The methods of preparing cone-tainers, adding Fusarium (isolates of all four species) to the growing mix, treating seed with BCAs and greenhouse cultivation were the same as in Example 1. The method of inoculating the cone-tainers with ectomycorrhizal fungi were the same as in Example 2. Each of the biological control agents which were effective against Fusarium root rot in the studies described in Example 1 were evaluated eleven months after sowing. Determination of root volume was by a determination of the weight of the water displaced by the root mass. The results of studies using the claimed BCAs and Mycostop® with the two newly isolated ectomycorrhizal fungi are shown in Table 3. The non-mycorrhizal biological control agents were quite effective by themselves as biological control agents. As disclosed in Example 1 supra, Mycostop® was not effective when used as a single-application seed coat. Effective results were only achieved by repeated Mycostop® treatments. The claimed BCAs were effective as shown with a single treatment, however. Thus, the claimed BCAs are superior to the prior art because they are more effective than a successful commercial product. In combination with Hebeloma, these agents were even more effective than when used alone in controlling root rot. The Hebeloma by itself was ineffective under these conditions in becoming established in a mycorrhizal relationship and in controlling Fusarium root rot. However, the combination of the Hebeloma and the BCAs were more effective than the BCAs alone or in combination with Laccaria in preventing root rot. Indeed, since, under these conditions, Hebeloma alone was ineffective as an ectomycorrhizae and in reducing Fusarium root rot, one would expect the combination of Hebeloma with the bacterial agents to be no better than the bacterial agents alone. However, the Hebeloma/BCA combinations were much more effective than the Laccaria/BCA combinations, even though the Laccaria alone was somewhat effective. Therefore, the bacterial

TABLE 2

Growth chamber evaluation of ectomycorrhizal fungi for biocontrol of Fusarium root rot.[1]

| Fusarium Added | Mycorrhizal Treatment | Mean Root Rot Severity | | % Healthy Seedlings | | % Roots Ectomycorrhizal | |
|---|---|---|---|---|---|---|---|
| − | Hebeloma | 1.1 | c | 89 | a | 65 | a |
| − | Laccaria | 1.1 | c | 94 | a | 46 | b |
| + | Hebeloma | 1.6 | b | 68 | a | 63 | a |
| + | Laccaria | 2.7 | a | 14 | b | 21 | c |
| + | none | 2.5 | a | 7 | b | 1 | d |

[1]Data followed by the same letters are not significantly different at $P = 0.05$.

Example 3

Combinations of the non-mycorrhizal ECAs and the ectomycorrhizal fungi disclosed herein were evaluated for effectiveness in: a) establishing an ectomycorrhizal infection and b) controlling Fusarium root rot on eastern white pine.

agents were unexpectedly effective in combination with Hebeloma. The Hebeloma-bacterial agent combination is thus the most effective of any known treatments in establishing mycorrhizal infections. This superiority is reflected in some cases by the significant increases in root volume of the combinations.

TABLE 3

Greenhouse evaluation of ectomycorrhizal and bacterial agent combinations.[1]

| Mycorrhizal Treatment | Bacterial Agent | Mean Root Rot Severity | | % Healthy Seedlings | % Roots Ectomycorrhizal | | Root Volume (g) | |
|---|---|---|---|---|---|---|---|---|
| Hebeloma arenosa | 5a | 1 | f | 100 | 43 | bc | 1.5 | bcde |
| | 19b | 1.4 | cdef | 79 | 46 | bc | 2.1 | abc |
| | 176 | 1 | f | 100 | 65 | a | 2.5 | a |
| | Mycostop | 1 | f | 100 | 65 | a | 2.4 | ab |
| | None | 2.2 | ab | 18 | 6 | fgh | 0.9 | e |
| Laccaria | 5a | 1.4 | cdef | 69 | 16 | efgh | 1.7 | abcde |
| | 19b | 2.4 | a | 23 | 14 | efgh | 1.4 | cde |
| | 176 | 1.8 | bcdef | 57 | 24 | de | 1.6 | bcde |
| | Mycostop | 1.8 | bcdef | 41 | 33 | cd | 1.1 | de |
| | None | 1.4 | cdef | 63 | 21 | def | 1.2 | cde |
| None | 5a | 1.8 | bcde | 42 | 4 | gh | 1.2 | cde |
| | 19b | 1.9 | bcde | 24 | 3 | gh | 1.4 | cde |
| | 176 | 2.1 | bc | 13 | 2 | gh | 1.1 | de |
| | 19 | 2.5 | a | 62 | 2 | gh | 1.5 | bcde |
| | 20 | 1.3 | def | 67 | 1 | h | 1.1 | de |
| | Mycostop | 2.1 | bcd | 17 | 6 | fgh | 1.2 | cde |
| | None | 2.5 | a | 0 | 1 | gh | 0.8 | e |

[1]Data followed by the same letters are not significantly different at $P = 0.05$.

What is claimed is:

1. A method for reducing the incidence of Fusarium spp. infection in conifer seedlings grown from conifer seeds comprising contacting said conifer seeds with a culture of a bacterial control agent inhibitory to the growth of Fusarium spp., wherein said culture of a bacterial control agent is selected from the group consisting of *Methylbacterium mesophilicum, Streptomyces lavendulae, Streptomyces rochei, Streptomyces violaceusniger*, and a mixture of *Rhodococcus erythropolis, Kocuria varians*, and *Pseudomonas diminuta*, and combinations thereof, drying said culture of a bacterial control agent onto the surface of said conifer seeds to form a protective coating thereon, planting said seeds in a plant-growth medium, and treating said plant-growth medium with a culture of Hebeloma spp.

2. A method for reducing conifer seedling root rot and damping off in conifer seedlings grown from conifer seeds comprising contacting said conifer seeds with a culture of a bacterial control agent inhibitory to the growth of Fusarium spp., wherein said culture of a bacterial control agent is selected from the group consisting of *Methylbacterium mesophilicum, Streptomyces lavendulae, Streptomyces rochei, Streptomyces violaceusniger*, and a mixture of *Rhodococcus erythropolis, Kocuria varians*, and *Pseudomonas diminuta*, and combinations thereof, drying said culture of a bacterial control agent onto the surface of said conifer seeds to form a protective coating thereon, planting said seeds in a plant-growth medium, growing said seeds in the plant-growth medium until a nascent root emerges from at least one seed, and treating said nascent root with a culture of Hebeloma spp.

3. The method of claim 1 or 2, wherein said culture of Hebeloma spp is a culture of *Hebeloma arenosa*.

4. The method of claim 2, wherein the nascent root is treated by adding the culture of Hebeloma spp. to the plant-growth medium.

5. The method of claim 2, wherein the nascent root is treated by transplanting the at least one seed with a nascent root into a soil inoculated with the culture of Hebeloma spp.

* * * * *

UNITED STATES PATENT AND TRADEMARK OFFICE
CERTIFICATE OF CORRECTION

PATENT NO.: 6,133,196
DATED: Oct. 17, 2000
INVENTOR(S) : Ocamb et al.

It is certified that error appears in the above-identified patent and that said Letters Patent is hereby corrected as shown below:

In column 4, line 14, delete the comma after "*mesophilicum*".

In column 4, line 17, delete "28140" and insert --21840--, therefor.

In column 6, line 44, delete "agents)are" and insert --agents) are--, therefor.

In column 8, line 12, delete "ECAs" and insert --BCAs--, therefor.

In column 10, line 19, insert --NRRL B-21842-- after "*mesophilicum*".

In column 11, line 12, delete "Laccaria bicolor" and insert --*Laccaria bicolor*--, therefor.

In column 11, line 56, delete "ECAs" and insert --BCAs--, therefor.

Signed and Sealed this

First Day of May, 2001

*Attest:*

NICHOLAS P. GODICI

*Attesting Officer*    *Acting Director of the United States Patent and Trademark Office*